US006986988B2

(12) United States Patent
Gilad et al.

(10) Patent No.: US 6,986,988 B2
(45) Date of Patent: Jan. 17, 2006

(54) METHOD FOR ENRICHMENT OF NATURAL ANTISENSE MESSENGER RNA

(75) Inventors: Shlomit Gilad, Gedera (IL); Paz Einat, Ness-Ziona (IL); Avital Grossman, Ness-Ziona (IL)

(73) Assignee: Quark Biotech, Inc., Pleasanton, CA (US)

( * ) Notice: Subject to any disclaimer, the term of this patent is extended or adjusted under 35 U.S.C. 154(b) by 808 days.

(21) Appl. No.: 09/833,031

(22) Filed: Apr. 11, 2001

(65) Prior Publication Data

US 2004/0180336 A1 Sep. 16, 2004

Related U.S. Application Data

(63) Continuation-in-part of application No. 09/680,420, filed on Oct. 6, 2000, now Pat. No. 6,528,262.
(60) Provisional application No. 60/157,843, filed on Oct. 6, 1999.

(51) Int. Cl.
C12Q 1/68 (2006.01)
C12P 19/34 (2006.01)

(52) U.S. Cl. .................. 435/6; 435/91.2; 435/91.21; 435/91.51; 536/23.1; 536/24.1; 536/24.5
(58) Field of Classification Search .............. 435/6, 435/91.2, 91.21, 91.51; 536/23.1, 24.1, 24.5
See application file for complete search history.

(56) References Cited

U.S. PATENT DOCUMENTS 5,891,636 A  *  4/1999  Van Gelder et al. ............ 435/6

FOREIGN PATENT DOCUMENTS

WO  WO 99/27113   6/1988
WO  WO 99/60164   11/1999

OTHER PUBLICATIONS

Vanhee–Brossollet et al, "Do natural antisense transcripts make sense in eukaryotes?", *Genie* 211:1–9 (1998).
XP–002171236 –Dolnick, "Cloning and characterization of a naturally occurring antisense RNA to human thymidylate synthase mRNA", *Nucleic Acids Research*, 21(8) 1747–1752 (1993).

* cited by examiner

*Primary Examiner*—John L. LeGuyader
*Assistant Examiner*—JD Schultz
(74) *Attorney, Agent, or Firm*—Browdy and Neimark, PLLC

(57) ABSTRACT

A method for enrichment of natural antisense mRNA which involves hybridization of cDNA obtained from sense RNA with cDNA obtained from antisense RNA, followed by DNA polymerase treatment of the sense-antisense hybrid DNA molecule. A natural antisense library can be generated by cloning of sense-antisense hybrid DNA molecules in a vector.

18 Claims, 5 Drawing Sheets

METHOD FOR ENRICHMENT OF NATURAL ANTISENSE MESSENGER RNA

CROSS-REFERENCE TO RELATED APPLICATIONS

The present application is a continuation-in-part of application Ser. No. 09/680,420, filed Oct. 6, 2000, now U.S. Pat. No 6,528,262, which claims priority under 35 U.S.C. §119 (e) from U.S. provisional application No. 60/157,843, filed Oct. 6, 1999, the entire contents of both applications being hereby incorporated herein by reference.

BACKGROUND OF THE INVENTION

1. Field of the Invention

The present invention relates to a method for enriching antisense messenger RNA that are naturally expressed in cells.

2. Description of the Related Art

The functional information of the genes in the genome is unidirectional. Taking as an example the most simple gene which encodes a protein, the RNAs encoding a protein are transcribed from one of the strands and define one mRNA that possesses the information for the translation of a single protein. This simplistic view is obviously more complex for many genes due to mechanisms such as alternative splicing and intron encoded mRNAs. While this general view of the unidirectional nature of genes is true with regard to structural information, it is not so with regard to regulatory information. The possibility of transcription of the other strand of a gene, in the reverse direction, will result in the production of an RNA that is complementary to the mRNA that possesses the structural information (the sense mRNA). Such RNAs, termed antisense RNAs, have the potential to strongly bind to the sense mRNA, producing a double stranded RNA, and to inhibit the realization of the structural information. However, it is possible that these RNAs also possess structural information.

In general, natural antisense RNAs are endogenous transcripts containing regions complementary to transcripts of other genes or other transcripts arising from the same gene locus. Antisense RNA is an RNA which contains a stretch of nucleotides complementary to another RNA that has some cellular function. The length of the complementary stretch is usually a few hundred nucleotides, but shorter stretches can also be important. The expression of antisense RNA is a powerful way of regulating the biological function of the sense RNA molecules. Natural antisense RNAs have been shown to play important regulatory roles, including control of cell growth, malignant transformation and other cellular phenotypes. Through the formation of a stable duplex between the sense RNA and antisense RNA, the normal or sense RNA transcript can be rendered inactive and untranslatable.

Natural antisense transcripts can either be cis-encoded or trans-encoded. Cis-encoded antisense arises from transcription of the complementary strand of the sense gene; both sense and antisense transcripts originate from the same locus and thus, the antisense transcripts have regions of perfect complementarity to the sense mRNA. Trans-encoded antisense arises from transcription of a different genomic locus, and accordingly, it is expected that in such cases the complementarity of the antisense region will be not complete.

Following the discovery of natural antisense RNAs in prokaryotes, natural antisense RNAs were also discovered in a variety of eukaryotes covering a wide range of the phylogenetic tree, including viruses (Michael et al., 1994), slime molds (Lee et al., 1993), insects (Lankenau et al., 1994), amphibians (Kimelman et al., 1989), birds (Farrell et al., 1995) and mammals (Murphy et al., 1994). Moreover, most of the genes for which endogenous antisense transcripts were discovered encode proteins of key regulatory roles in important cellular phenotypes, such as cellular proliferation (Chang et al., 1991), apoptosis (Khochbin et al., 1989) and embryonic development (Bedford et al., 1995), or of key cellular processes such as translation (Noguchi et al., 1994), transcription (Krystal et al., 1990) and splicing (Fu et al., 1992). The thorough review article by Vanhee-Brossollet and Vaquero (1998) offer a summary of all antisense RNAs discovered so far and their functional importance. The evidence suggests that control of gene expression by endogenous antisense RNAs is one of the regulatory mechanisms in the cell and is widespread throughout the eukaryotic kingdom.

All of the antisense transcripts discovered so far were found by sporadic experiment stemming from studies of single genes. This implies that the antisense regulatory mechanism might be of general importance and relevant for many more genes. Thus, a general method for finding those mRNAs in the cell for which an antisense RNA exists would be of great value. The object of the approach and method of the present invention is to enable those in the art to investigate which mRNAs in the cell have antisense RNAs, as compared to studies done up until now which investigated the question "does this specific mRNA have an antisense RNA counterpart?"

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is directed to rapid methods for enrichment of natural antisense mRNA (the exonuclease and polymerase activities of DNA polymerases on the sense-antisense double-stranded hybrid), followed by amplification and cloning of its corresponding cDNA. Thus, the invention overcomes the deficiencies in the prior art as discussed above. These methods provide for the enrichment and detection of natural antisense mRNA from any natural source of RNA. Poly A+ mRNA in a sample of RNA is converted into single-stranded cDNA which is denatured to disrupt any secondary structure, and then allowed to re-anneal under stringent conditions with any other cDNA having a segment with a significant complementary sequence to form a hybrid molecule with a double-stranded cDNA segment. Sense and antisense cDNAs hybridize to each other and form double-stranded stretches or segments of DNA. In an embodiment of the present invention, the resulting hybridization products with double-stranded DNA segments are treated with a DNA polymerase, such as T4 DNA polymerase, which has a 5' to 3' polymerase activity and a 3' to 5' exonuclease activity. The resulting double-stranded molecules are then amplified and cloned.

DETAILED DESCRIPTION OF THE INVENTION

The present invention is based on the development of simple and rapid methods for the enrichment of natural antisense mRNA from any source of mRNA. The source of the poly A+ mRNA used in the present method can be a cell line, tissue, whole organism, or even a mixture of poly A+ mRNA from two or more sources. The source(s) of mRNA is preferably a natural source(s). A mixture of RNA from different sources can be, for example, a mix of control mRNA derived from normal tissue or cells and mRNA from treated tissues or cells, or a mix of control mRNA and mRNA derived from pathologic tissue mRNA, etc.

Figure 1:
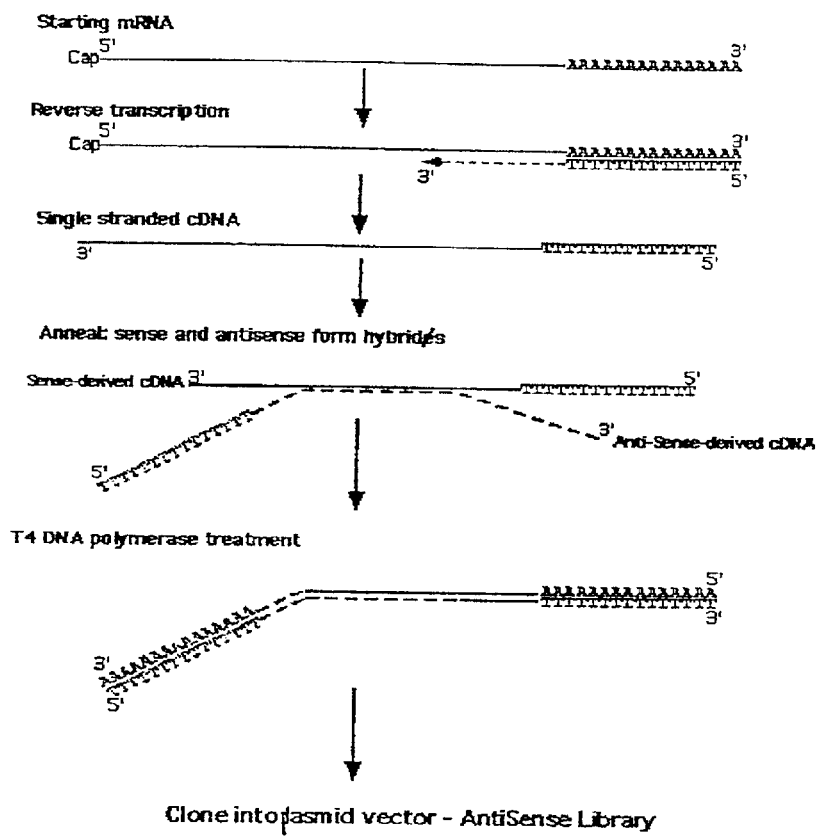
FIG. 1 shows a schematic presentation of an embodiment of the natural antisense enrichment procedure according to the present invention.

A method for enrichment of natural antisense messenger RNA (mRNA) according to the present invention is schematically presented in FIG. 1. A population of single-stranded cDNA molecules is generated from a source of poly A$^+$ RNA (RNA recovered from oligo dT columns after loading thereon a sample of total RNA from cells or tissue), where such columns bind the mRNA that contain a polyA stretch. The vast majority of eukaryotic mRNA have polyA tails at their 3'-end. The RNA that does not contain polyA is washed away and the bound RNA is recovered. The result is an RNA sample enriched for the polyA-containing mRNAs. The polyA$^+$ RNA is used as starting mRNA template for reverse transcription from an oligonucleotide primer. The oligonucleotide primer contains polydeoxythymidine (oligo dT) which can anneal to the poly A+ tail of mRNA, and also preferably contains one or more restriction enzyme cleavage sites for later use in cloning into vectors, and a further "END" sequence at the 5'-end of the primer that allows specific amplification.

The population of cDNA molecules generated by reverse transcription with a reverse transcriptase is heated to disrupt any secondary structure, such as self-annealing, and then incubated under stringent conditions to allow hybridization of complementary cDNA segments. It is expected that a cDNA (antisense) complementarity to the sense cDNA will form an at least partially double-stranded hybrid molecule. cDNA generated from cis-encoded antisense mRNA, which arises from transcription of the complementary strand of the sense gene, will have a certain region of perfect complementarity to its corresponding sense cDNA. However, cDNA generated from trans-encoded antisense, which arises from transcription of a different genomic locus, is expected to have only partial complementarity to a sense cDNA from a different genomic locus. Even in such a case, functional trans-encoded antisense will generate a double-stranded structure stable enough to be retained by the enrichment method.

Treating the hybrid molecule, which is at least partially double-stranded, with a DNA polymerase having 5' to 3' polymerase activity and 3' to 5' exonuclease activity produces double-stranded molecules with complete complementarity. This treatment with DNA polymerase cleaves single-stranded DNA molecules with free 3' ends until the DNA polymerase reaches a region of stable double-stranded structure, producing a DNA molecule with a double-stranded region and one or two adjacent single-stranded DNA regions with free 5' ends. This serves as a template for the 5' to 3' polymerase activity of the enzyme which produces a final product with blunt ends. The DNA polymerase having 3' to 5' polymerase activity useful in the method according to the present invention is preferably T4 DNA polymerase. Four other enzymes useful in the method according to the present invention are Platinum Pfx DNA polymerase and Deep Vent DNA polymerase (both from New England Biolabs, Beverly, Mass.), Pwo DNA polymerase (Roche) and Pfu DNA polymerase (Stratagene, La Jolla, Calif.). Other polymerases can be used, including but not limited to any suitable DNA polymerase having both aforesaid activities.

The double-stranded molecules resulting from the DNA polymerase reaction are amplified by the polymerase chain reaction (PCR) using a polymerase, such as Taq DNA polymerase, or other thermostable polymerases, and preferably with a primer identical to the END region of the poly dT-containing oligonucleotide primer previously used to generate the population of cDNA. Thus, natural antisense mRNA molecules as converted to double-stranded cDNA molecules are enriched. The amplified double-stranded DNA molecule enriched for natural antisense mRNA can be easily cloned into a vector using one or more restriction enzyme cleavage sites at the ends thereof (i.e., derived from the oligonucleotide primer). Confirmation that the cloned double-stranded cDNA encodes a natural antisense mRNA can be obtained by RT-PCR or Northern blot analysis as described in the Example 1 herein.

The oligonucleotide primer used for amplifying the double-stranded molecules from the DNA polymerase reaction is complementary to and preferably identical to the END sequence located at the 5'-end of the polydT primer for initially generating the double-stranded molecules. The location of the END sequence before (5' to) the restriction enzyme cleavage site(s) and polydT region) only amplifies the correct template and gives rise to products that have the restriction enzyme cleavage site(s) available for cloning. Thus, natural antisense molecules can only be enriched and amplified if there is a successful polymerization which produces templates that can be amplified by the Endogenous Antisense Identification (EASI) procedure of the present invention.

Because natural antisense RNAs have been shown to play important regulatory roles or provide new regulatory information for known genes in the control of cell growth, malignant transformation, and other cellular phenotypes, the present method provides a basis for finding new genes with important cellular regulatory roles or new regulatory information for known genes and provides a starting material for development of an antisense-based therapeutic to treat a disease or disorder in which the down-regulation or inhibition of the sense gene or transcript is sought.

The EASI method allows production of a cDNA population enriched for sequences representing endogenous antisense RNAs. In Example 1, one approach to use the method for the identification of the antisense RNA is described. This employs the derivation of cDNA libraries from the EASI enriched cDNA population, followed by sequencing of cDNA clones, characterization of the sequences, and analysis of the existence of antisense RNA in the cells. Example 2 describes a way to use the EASI enriched cDNA population to derive probes for microarray analysis, which allows both the detection of antisense transcripts and their differential expression. While the specific RNA polymerase disclosed in Example 2 below is T7 RNA polymerase, this specific RNA polymerase can be any bacteriophage RNA polymerase which uses DNA as template to produce RNA, such as T7 RNA polymerase, T3 RNA polymerase, SP6 RNA polymerase, etc.

Having now generally described the invention, the same will be more readily understood through reference to the following examples which are provided by way of illustration and is not intended to be limiting of the present invention.

EXAMPLE 1

The antisense enrichment procedure according to the present invention, also designated as the Endogenous Antisense Identification (EASI) procedure, was applied to a human glioma cell line and shown in experiments to enrich for antisense mRNA/cDNA known to have a natural antisense mRNA. The experimental results and the materials and methods used in the experiments discussed in this example are provided below.

Materials and Methods
cDNA First Strand Synthesis:

Two µg of poly A+ RNA from human A172 glioma cell line were diluted with double distilled water (DDW) up to 6 µl volume. Secondary structure formation or self-annealing of RNA molecules is disrupted by incubation at 80° C. for 2 min and then quick chilled on ice. 4 µl of a 10 mM oligo dT (deoxythymidine) primer, which contains cloning/cleavage sites for the NotI restriction enzyme and has the sequence
5'-TTCTAGAATTCAGCGGCCGC(T)$_{18}$N$_{1\ (G,A,C)}$N$_{2\ (G,A,C,T)}$-3' (SEQ ID NO:1)
(where 5'-TTCTAGAATTCAGCGGCCGC-3', corresponding to nucleotides 1 to 20 of SEQ ID NO:1, is termed the "END" sequence), 4 µl of 5× Superscript buffer, 1 µl of RNasin, 2 µl of 0.1M DTT (dithiothreitol) and 2 µl of 10 mM dNTPs (deoxynucleoside 5'-triphosphates) were added to the poly A+ RNA. After preheating at 42° C., 1 µl of RT Superscript enzyme was added and incubated at 42° C. for 1.5 hours. The reaction mixture was then heated to 80° C. for 2 min and the RNA strands were digested with alkaline treatment, followed by neutralization.

Hybridization:

The cDNA generated was precipitated and then resuspended with 30 µl hybridization buffer (40 mM PIPES, pH 6.4, 1 mM EDTA, pH 8.0, 0.4 M NaCl, 80% formamide, DDW). Any secondary structure was disrupted at 85° C. for 10 min and then the cDNA was rapidly transferred to a 52° C. bath for 16 hours. After 16 hours of incubation, the cDNA was precipitated with ethanol and resuspended in 30 µl DDW.

T4 DNA Polymerase Treatment:

Blunt ending by both removal of single-stranded cDNA 3' to 5' and extension of double-strand over a single-stranded template was done on 30 µl of hybridized cDNA molecules with T4 DNA Polymerase (3–6 units), dNTPs, T4 reaction buffer, and BSA (bovine serum albumin) to a final volume of 80 µl. After reacting for 1 hour at 16° C., 5 µl of Klenow sequencing grade enzyme was added and then transferred for 30 min at an incubation temperature of 37° C. The inactivation of the enzymes was carried out at 75° C. for 10 min, followed by phenol/chloroform extraction and EtOH precipitation. The precipitated pellet was resuspended in 12 µl of DDW for use as the PCR template in the next PCR amplification step.

Platinum Pfx DNA Polymerase Treatment

Blunt ending by both removal of single-stranded cDNA 3' to 5' and extension of double-strand over a single-stranded template was done on 30 ml of hybridized cDNA molecules with 1 ml of Platinum Pfx DNA polymerase (2.5 u/ml), 1.5 ml 10 mM dNTPs, 5ml 10× Pfx Amplification buffer, 1 ml 50 mM MgSO2 and 11.5 ml DDW to a final volume of 50 ml and then transferred for incubation at 72° C. for 5 min. The inactivation of the enzymes was carried out at 75° C. for 10 min, followed by phenol/chloroform extraction and EtOH precipitation. The precipitated pellet was resuspended in 12 ml of DDW for use as the PCR template in the next PCR amplification step.

Deep Vent DNA Polymerase Treatment

Blunt ending by both removal of single-stranded cDNA 3' to 5' and extension of double-strand over a single-stranded template was done on 30 ml of hybridized cDNA molecules with 2 ml 10 mM dNTPs, 5 ml 10× Thermo polymerase reaction buffer, 2 ml 100 mM MgSO2 and 10 ml DDW to a volume of 49 ml and preincubated at 72° C. for 2 min. 1 ml of Deep Vent DNA polymerase (2 u/ml) was added and the whole mixture was transferred for incubation of the reaction at 72° C. for 5 min. The inactivation of the enzymes was carried out at 75° C. for 10 min, followed by phenol/chloroform extraction and EtOH precipitation. The precipitated pellet was resuspended in 12 ml of DDW for use as the PCR template in the next PCR amplification step.

Pwo DNA Polymerase Treatment

Blunt ending by both removal of single-stranded cDNA 3' to 5' and extension of double-strand over a single-stranded template was done on 30 ml of hybridized cDNA molecules with 2 ml 10 mM dNTPs, 5 ml 10×PCR buffer with 20 mM MgSO2 and 12 ml DDW to a volume of 49 ml and then transferred for preincubation at 72° C. for 2 min. Then 1 of Pwo DNA polymerase (5 u/ml) was added and the whole mixture was transferred for incubation at 72° C. for 5 min. The inactivation of the enzymes was carried out at 75° C. for 10 min, followed by phenol/chloroform extraction and EtOH precipitation. The precipitated pellet was resuspended in 12 ml of DDW for use as the PCR template in the next PCR amplification step.

Pfu DNA Polymerase Treatment

Blunt ending by both removal of single-stranded cDNA 3' to 5' and extension of double-strand over a single-stranded template was done on 30 ml of hybridized cDNA molecules with 5 ml cloned Pfu DNA polymerase (2.5 u/ml), 5 ml 10 mM dNTPs, 5 ml 10× cloned Pfu polymerase buffer, and 5 ml DDW to a final volume of 50 ml and then transferred for incubation at 72° C. for 5 min. The inactivation of the enzymes was carried out at 75° C. for 10 min, followed by phenol/chloroform extraction and EtOH precipitation. The precipitated pellet was resuspended in 12 ml of DDW for use as the PCR template in the next PCR amplification step.

PCR Amplification:

1 µl from the resuspended DNA pellet resulting from the T4 DNA polymerase treatment was used as a template for PCR amplification with the same END primer derived from the oligo dT primer used for the initial cDNA synthesis. The PCR conditions are as follows: The reaction was performed in a total volume of 50 µl with 1 µl template after blunting (T4 DNA polymerase treatment), 5 µl Boehringer 10× buffer 2, 1 µl 10 mM dNTPs, 4 µl 10 µM primer, 0.5 µl PERFECT MATCH PCR enhancer (Stratagene) La Jolla, Calif., 0.5 µl of (3.5 u/µl) Boehringer Taq high fidelity DNA polymerase (Boehringer-Mannheim) and DDW for the remaining volume. The temperature program used for PCR was as follows: 2 min of 94° C. for denaturation and 16 cycles of: denaturation at 94° C. for 30 sec, annealing at 64° C. for 30 sec, and extension at 72° C. for 4 min. At the end of the cycling, the extension was completed at 72° C. for 7 min.

Cloning:

The PCR amplified product was digested with NotI and ligated into pBLUESCRIPT vector (Stratagene) linearized with the restriction enzyme Eag1. EagI-cleaved sticky ends are compatible with NotI-cleaved sticky ends.

µl of RNAseOut (40 units/µl), 2 µl of 10 mM dNTPs and 1 µl H$_2$O. 1 µl of Thermoscript RT (15 units/µl) was added and the reaction was carried out at 60° C. For 1 hour. The reaction was then terminated by incubation at 85° C. For 5 minutes with the RNA being removed by the addition of 1 µl of RNAseH (1 u/µl; Boehringer) and incubation at 37° C. For 20 minutes.

The PCR amplication reaction was conducted under standard conditions using a pair of sense and antisense primers for the tested gene. Taq DNA polymerase from Boehringer was used. The initial cycle consisted of incubation at 94° C. For 3.5 minutes followed by 5 cycles of: denaturation at 94° C. For 30 seconds, annealing at 62° C. For 30 seconds and extension at 72° C. For 2 minutes. This was then followed by 25 cycles of: 94° C. For 30 seconds, 58° C. For 30 seconds and 72° C. For 2 minutes. The reaction was terminated with a step of incubation at 72° C. For 7 minutes.

Primers and Sequences

The primers and sequences used in the EASI procedure described and exemplified in this example are provided below.

| | | | |
|---|---|---|---|
| Human c-erb | | | |
| | ERB-SEN2: | 5'-GATGGGAGTTGTGTGTTTAGTC-3' | (SEQ ID NO:2) |
| | ERB-RC: | 5'-GGAGAGAGAAGTGCAGAGTTCG-3' | (SEQ ID NO:3) |
| Human ku autoantigen | | | |
| | KU_FOR: | 5'-TTAGTACAAACTTAGGGCTCT-3' | (SEQ ID NO:4) |
| | KU_REV: | 5'-TCATGGCAACTCCAGAGCAG-3' | (SEQ ID NO:5) |
| Human GAPDH | | | |
| | GAPDH_FOR: | 5'-ACCACAGTCCATGCCATCAC-3' | (SEQ ID NO:6) |
| | GAPDH_REV: | 5'-TCCACCACCCTGTTGCTGTA-3' | (SEQ ID NO:7) |
| Human RbAp48 (clone N1–15) | | | |
| | N1-15FOR: | 5'-GGAGTTAGTCCTTGACCACTAG-3' | (SEQ ID NO:8) |
| | N1-15RC: | 5'-GCACTTACACAGTTAGTCATGG-3' | (SEQ ID NO:9) |
| Sequence of clone N1–15- | designated SEQ ID NO:10 | | |

The transformants were detected in the presence of X-Gal (5-bromo-4-chloro-3-indolyl β-D-galactopyranoside) and IPTG (isopropyl β-D-thiogalactopyranoside). White colonies containing inserts were sequenced following miniprep DNA purification. All the sequencing products were analyzed by common Bioinformatic programs, such as BLAST, and the interesting sequences were used as templates for single-stranded probes for Northern blot analysis to confirm the presence of an antisense molecule.

A real antisense is determined to be present by use of two reverse complementary single-strand (ss) probes, each complementary to a different strand. For a known gene, the ss probe complementary to the sense strand will hybridize to the sense mRNA and give a signal on a Northern blot to a band of expected size. The ss probe complementary to the antisense strand will give a signal on a Northern blot if an antisense mRNA is present in the RNA population.

Reverse Transcription—PCR Amplification

The following gene-specific RT-PCR conditions were found to be of high specificity to the targeted gene. Poly A+ selected mRNA (100 ng) was used as template and the reactions were carried out with the Thermoscript RT enzyme (100 ng polyA+) (Gibco/BRL). RNA, 4 µl of 5× buffer, 10 µM primer and H$_2$O were mixed to a final volume of 14 µl. The mixture was incubated at 85° C. for 1 minute and then at 65° C. for 5 minutes. The following were then added while the tube was held at 60° C.: 1 µl of 0.1 mM DTT, 1

Northern Hybridization Using Single-stranded Probe

For each interesting fragment that was obtained from the bioinformatic analysis, two primers, forward and reverse, that are suitable for the two ends of the fragment were prepared. Northern blots were prepared according to *CURRENT PROTOCOLS IN MOLECULAR BIOLOGY* by F. M. Ausubel et al, Chapter 4.a with 6 µg of poly A+ RNA per lane.

Synthesis of Labeled Single-stranded DNA Probes:

The cDNA insert of the tested gene (isolated by digestion or by PCR from the plasmid) was labeled using well-known labeling reactions with Klenow enzyme. A specific sense or antisense primer was used to drive the synthesis of the probe in the presence of radioactive nucleotides. Thus, only one strand (sense or antisense, depending on the primer used) was synthesized and labeled with radioactivity. For each gene, the sense and antisense probes were generated and used for hybridization on separate blots.

For the preparation of DNA template, 0.5–1 µg of template from a miniprep DNA isolation procedure was denatured with NaOH treatment and incubated for 5 min. at RT (room temperature), precipitated with NH$_4$Ac pH 5.2, yeast tRNA and 100% EtOH. After ethanol precipitation, the pellet was redissolved in 7 µl of DDW.

For the synthesis of labeled single strands, 50–100 ng of the denatured template DNA was mixed and annealed with 10 pmols of the appropriate primer in Klenow buffer (10 mM Tris-HCl, pH 7.5, 5 mM MgCl$_2$, 7.5 mM DTT), and incubated at two different temperatures, 15 min at 60° C. and then 15 min. at RT. α-$^{32}$P-dCTP (specific activity of 3000 ci/mmol), Klenow enzyme (5 units) and dATP, dTTP and dGTP nucleotide solution (0.5 mM final concentration) were then added to the annealing mix and incubated for 20 min. at 37° C. to incorporated label into the synthesized strand of DNA. Afterwards, "cold" (non-radioactive) dCTP was added and the reaction was further incubated for 15 min. at 37° C. The inactivation of the Klenow enzyme was carried out by incubation at 75° C. For 10 min. The purification of the probe was done on a SEPHADEX G-50 column.

Northern Blot Hybridization and Post-hybridization Processing

1–5×10$^6$ cpm of denatured labeled probe was added per 1 ml hybridization solution and incubated overnight at 65° C. Prehybridization was carried out for 30 min to 2 hours at 65° C. The Northern blot was washed 3 times in 2×SSC, 0.2% SDS for 7 min. at RT and then twice with high stringency washing solution that contain 0.1×SSC, 0.2% SDS for 15 min. at 60° C. The blot was then exposed onto X-Ray films.

Results and Discussion

The antisense enrichment procedure was applied to examine the possible involvement of antisense RNAs in the response of the human glioma cell line A172 to hypoxia stress. This is a cell line model for the response of glial cells in the brain to ischemic injury that can result from events such as stoke. To detect antisense mRNAs that are involved in the response of the cells to hypoxia conditions, poly A+ selected mRNA was obtained from cells grown under hypoxia conditions as well as from cells grown under normal conditions. Single-stranded cDNA prepared from the two mRNA pools were mixed in equal proportions and used as the basis for the antisense enrichment procedure.

Figure 2:
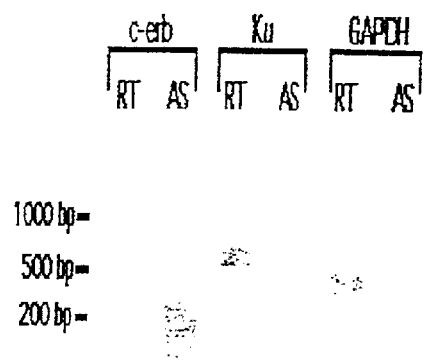
FIG. 2 shows an agarose gel electrophoresis analysis of PCR amplification products generated from single stranded cDNA obtained from reverse transcription (RT) of c-erb, Ku autoantigen, and GAPDH before and after the antisense enrichment procedure according to FIG. 1.

A gene, known to have an endogenous antisense mRNA was compared to two genes, for which no endogenous antisense mRNA is known to exist, to test the ability of the antisense enrichment procedure to enrich for antisense cDNAs. The presence of these three genes was tested before and after application of a preferred embodiment of the antisense enrichment method according to the present invention. As shown in FIG. 2, PCR amplification was performed for each gene with two gene specific primers, (1) before the antisense enrichment procedure on single strand cDNA (RT), and (2) is known to on DNA obtained after antisense enrichment (AS). The c-erb cDNA is known to be found at very low levels in the mRNA and gave no signal after PCR of normal RT products (20 ng poly A+ selected RNA). However, using a similar amount of DNA template, a strong signal was obtained from DNA obtained from the antisense enrichment procedure. The two other genes, Ku and GAPDH, for which there are no known antisense mRNA, and which are expressed at much higher levels, show a clear decrease in abundance in FIG. 2. This indicates that the antisense enrichment procedure according to the present invention advantageously enriches for cDNA for which a natural antisense counterpart exists (c-erb) in contrast to cDNA which lacks a natural antisense counterpart (Ku, GAPDH).

The final products of the antisense enrichment procedure were cloned as described in the materials and methods section and a library was created. After sequencing and bioinformatics analysis, few of the clones which matched known genes were chosen for further analysis to determine if they originated from an endogenous antisense mRNA. In order to examine the presence of antisense mRNAs to a specific gene, a gene specific RT-PCR method was established in which gene specific primers were used to initiate the reverse transcription reaction. To detect the normal (sense) transcript of a gene, an antisense primer was used. Conversely, when a sense primer was used, it should be possible to detect antisense mRNAs. It was found that standard RT-PCR reactions were not specific enough, and when a gene specific primer, either sense or antisense, was used, amplification products, for which no antisense transcript was known to exist for the gene, was observed. Moreover, other genes were also amplified. This indicates that standard RT-PCR reaction conditions resulted in non-specific reverse transcription of other mRNAs. A gene specific RT-PCR procedure was then established using highly specific conditions described in the Materials and Methods section of this example to confirm if the clones originated from natural antisense RNA. A highly specific RT reaction was performed with a sense primer (relative to the known sense mRNA) using Thermoscript reverse transcriptase (Gibco BRL).

Figure 3:
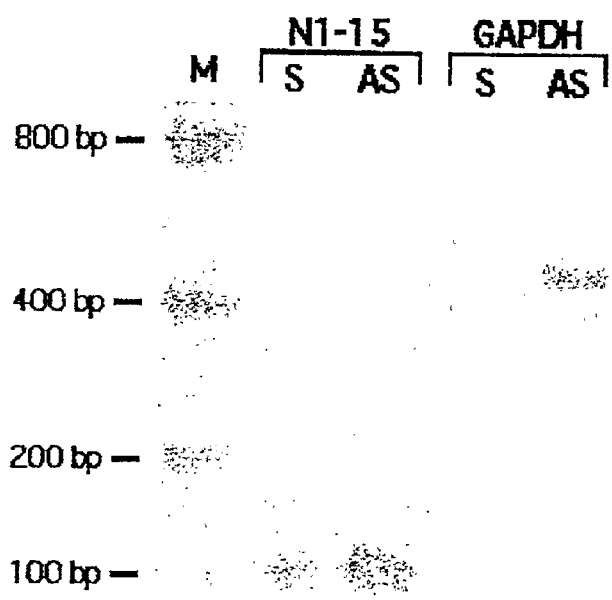
FIG. 3 shows gene-specific RT-PCR analysis of the expression of sense (S) and antisense (AS) mRNAs of clone N1-15 by use of specific primers complementary to the two strands, and GAPDH control by agarose gel electrophoresis. Clone N1-15 (RbAp48 mRNA encoding retinoblastoma binding protein, GenBank accession number X74262) was obtained from the antisense enrichment procedure. The lane designated M is a lane of molecular weight markers.

Under the aforesaid highly specific conditions such a reaction will result in a PCR product only if an antisense mRNA exists. This was compared to an RT reaction done using the antisense primer. Table 1 includes the list of clones from the antisense enriched library that were individually confirmed for the presence of matching antisense RNA. One clone, clone N1-15 (RbAp48 mRNA encoding retinoblastoma binding protein, accession number X74262), obtained from the antisense enrichment-derived library, is shown here in detail. A primer pair (sense and antisense primers) specific for the sequence obtained in the library was synthesized. Each primer was used to derive a RT reaction using Thermoscript reverse transcriptase. As a control, the same was done for GAPDH for which there is no known antisense mRNA. For both genes, the sense primer (S) is expected to support reverse transcription of antisense mRNA while the antisense primer (AS) is expected to support the synthesis of the sense (normal) mRNA. In FIG. 3, a clear signal was obtained with the sense primer (S) derived RT-PCR of the N1-15 clone whereas none was obtained (as expected) for the GAPDH mRNA. The antisense (AS)-derived RT-PCR however gave the expected products. This demonstrates that for clone N1-15, which matches the RbAp48 mRNA encoding retinoblastoma binding protein, PCR products of the expected size were obtained for both sense and antisense RT-PCR, whereas the control gene, GAPDH, which does not have any known antisense mRNA, resulted in a product only with the antisense primer. This suggested that an endogenous antisense mRNA does exist for this N1-15 gene.

TABLE 1

| Clone name | Gene name | Accession | Insert length | Match location | % identity | Strand-specific RT-PCR | Northern Blots Sense | Antisen | Bio informatics |
|---|---|---|---|---|---|---|---|---|---|
| N1_15 | RbAp48 encoding retinoblastoma binding protein | NM_005610 | 169 | 2179–2307 | 100 | Positive | 3.0 Kb | 3.5 Kb | Positive |

TABLE 1-continued

| Clone name | Gene name | Insert Accession | length | Match location | % identity | Strand-specific RT-PCR | Northern Blots Sense | Antisen | Bio informatics |
|---|---|---|---|---|---|---|---|---|---|
| N1_27 | CD9 antigen | NM_001769 | 550 | 621–1171 | 99 | Positive | ND | ND | |
| N1_33 | Thymosin b-10 | S54005 | 491 | 1–447 | 97 | Positive | 0.6 Kb | none | |
| N2_20 | Uncharacterized | AF187554 | 170 | 555–669 | 100 | Negative* | 7.0 Kb | 0.5 Kb | |
| N2_66 | 2–19 gene (downstream to G6PD) | X55448 | 206 | 42663–42866 | 99 | Positive | | | |
| N3_13 | Calumein | AF013759 | 143 | 2273–2415 | 100 | Positive | ND | ND | |
| D1-1 | SMRTE, Silencing mediator of retinoic acid and thyroid hormone receptor a | AF125672 | 111 | 8573–8667 | 96 | Positive | 8.5 kb | 3 kb | |
| D1-19 | M-phase phosphoprotein, mpp11 | X98260 | 100 | 578–661 | 98 | Negative | ND | ND | NO Antisense |
| D1-48 | Metallothionein 2 | X97260 | 189 | 225–327 | 98 | Positive | ND | ND | |
| D2-31 | Integrin a 3 | NM_005501 | 94 | 4421–4495 | 98 | Positive | 4.5 kb | 4.5 kb | |
| D2-3 | S100 calcium-binding protein A10 | NM_002966 | 161 | 549–649 | 100 | Negative | ND | ND | NO Antisense |
| D2-7 | Regulator of G-protein signaling 5 (RGS5) | AF030108 | 106 | 340–436 | 100 | Negative | ND | ND | NO Antisense |
| D2-20 | 14-3-3n | L20422 | 50 | 1524–1557 | 100 | Negative | ND | ND | NO Antisense |
| N26_3_50 | Ribosomal protein S11 | X06617 | 586 | 538–1 | 99 | Positive | ND | ND | Positive |
| Antisense gene | Human isocitrate dehydrogenase mRNA | U52144 | | | | | | | |
| N2_3_40 | *Homo sapiens* ribosomal protein S27 (metallopanstimulin 1) (RPS27) | NM_001030 | 363 | 1–329 (29–357) | 99 | Positive | ND | ND | Positive |
| Antisense gene | S24A Human ribosomal protein S24 mRNA | M31520 | | 249–353 (116–12) | 100 | | | | |
| N3_45 | UbA52 placental mRNA for Ubiquitin-52 fusion protein | X56999 | 563 | 52–552 | 99 | Positive | ND | ND | |
| 25_3_49 | *Homo sapiens* cDNA FLJ20494 fis, clone KAT08547 | AK000501 | 662 | 573–351: 352–24 | 95 | ND | ND | ND | Positive |
| | *M.musculus* mRNA for neuronal protein 15.6 | Y08702 | 504 | 449–329: 330–236: 186–104 | 86 | | | | |
| 20_2_33 | *Homo sapiens* actin, beta (ACTB) mRNA Matches to normal mRNA and to pseudogene. | NM_001101 | | 1326–1622 (19–315) 1688–1791 (382–485) | 97 | Positive | ND | ND | |

Figure 4:
FIG. 4 shows a Northern blot analysis of RbAp48 mRNAs with sense and antisense RbAp48 single stranded probes.

In order to determine if such an endogenous antisense mRNA indeed exists for the RbAp48 gene, a Northern blot analysis using sense and antisense single-stranded probes was performed. RNA from human A172 glioma cells grown under normal conditions or under hypoxia for 4 or 16 hours were separated by electrophosis on formaldehyde-agarose gels and blotted onto nylon membranes. One blot was hybridized with an antisense single stranded probe which should reveal the existence of any antisense RNA and a second blot was hybridized with the antisense probe to reveal the normal sense mRNA. As shown in FIG. 4, specific bands of different size hybridized with the different probes. These results demonstrate the existence of a mRNA species that hybridizes specifically with the sense probe and which is of a different size from the normal sense mRNA and further indicate that an endogenous antisense mRNA indeed exists for the RbAp48 gene. Interestingly, an inverted correlation is observed in the expression of the sense and antisense RbAp48 mRNAs under hypoxia, where the sense mRNA is reduced while the antisense mRNA is induced to higher levels, suggesting a regulatory role for the antisense RNA.

As can be seen from Table 1, 14 of the 18 tested clones were found to be positive under the experimental conditions or by bioinformatic analysis (clone 25-3-49). The bioinformatic analysis utilized the BLAST program (NCBI) to find matches between the clone and a certain region of another gene that is complementary to it. The analysis thus showed that the "EASI" antisense enrichment methodology is efficient.

Table 2 identifies the inserts in the clones listed in Table 1 by SEQ ID NO.

TABLE 2

| Insert from clone | SEQ ID NO: |
|---|---|
| N1_15 | 11 |
| N1_27 | 12 |
| N1_33 | 13 |
| N2_20 | 14 |
| N2_66 | 15 |
| N3_13 | 16 |
| D1-1 | 17 |
| D1-19 | 18 |
| D1-48 | 19 |

TABLE 2-continued

| Insert from clone | SEQ ID NO: |
|---|---|
| D2-31 | 20 |
| D2-3 | 21 |
| D2-7 | 22 |
| D2-20 | 23 |
| N26-3-50 | 24 |
| N2-3-40 | 25 |
| N3-45 | 26 |
| 25-3-49 | 27 |
| 20-2-33 | 28 |

EXAMPLE 2

Figure 5:
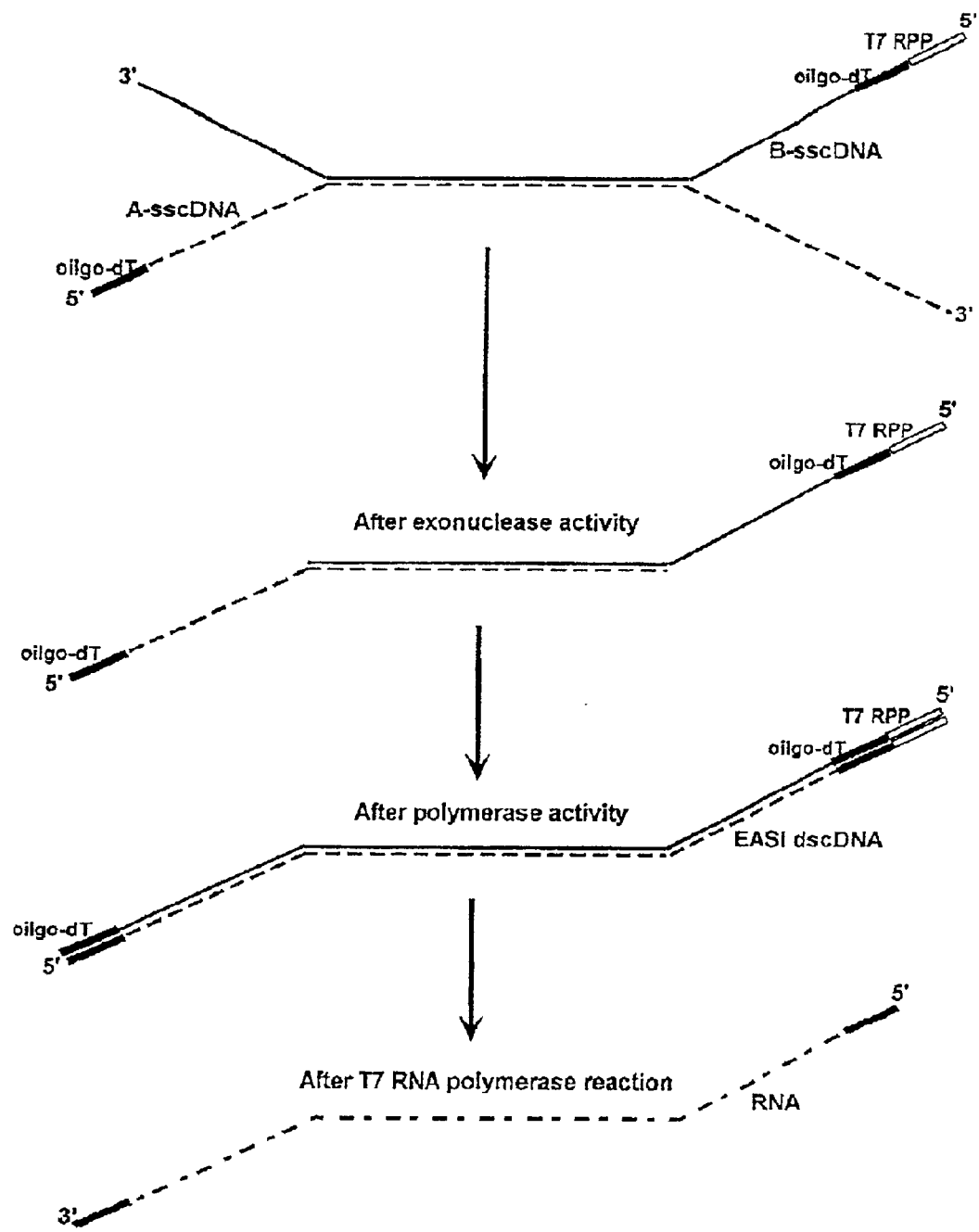
FIG. 5 shows a schematic presentation of a second embodiment of the natural antisense enrichment procedure according to the present invention.

To produce probes for microarray analysis from the EASI enriched cDNA, the following procedure may be used (graphically represented in FIG. 5) RNA is derived from cell population A (A-RNA) and from cell population B (B-RNA). A reverse transcription reaction with regular oligo-dT is used to make single stranded cDNA from A-RNA (A-sscDNA). For B-RNA an oligo-dT that has an additional sequence of the T7 RNA polymerase promoter region is used (e.g., SEQ ID NO:29). This produces a single stranded cDNA population (B-sscDNA) that has the T7 RNA polymerase promoter (T7RPP) region at its 5' end. Using the regular EASI method described in Example 1, the A-sscDNA and B-sscDNA populations are mixed, and allowed to anneal to each other. A DNA polymerase that also has a 3' to 5' exonuclease activity is then used (e.g., T4 DNA polymerase) to enrich for the population of cDNA that annealed to each other. The result of this reaction is a chimeric double stranded cDNA that has the T7 RPP on one of its ends. This now becomes the template for a T7 RNA polymerase reaction. The RNA produced from this reaction can now be labeled with a fluorescent dye for DNA microarray analysis using standard methods.

It should be noted that only in the cases where an antisense RNA is over-expressed in one population (e.g., A-RNA), and its complementary sense mRNA is over-expressed in the second population (e.g., B-RNA), will the T7RPP be on only one end of the double stranded cDNA template. If sense and antisense RNAs are found in the same population (B-RNA), they will anneal to each other and the resulting double stranded cDNA will have the T7 RNA polymerase promoter region on both ends. Such a template will cause production of both sense and antisense RNA that will cancel each other during hybridization. Thus, significant labeling is produced only in cases where there is differential expression of the antisense RNAs.

For hybridization to DNA microarrays, the EASI T7RP derived RNA can be labeled with one fluorescent die (e.g., Cy3). This probe can be compared to a probe derived from A-RNA or from B-RNA. Such a probe will be labeled with another fluorescent dye (e.g., Cy5). After hybridization to the DNA microarray, differentially expressed antisense RNA can be detected by simple analysis of the hybridization results. Since the EASI T7RP derived probe enriches for cases in which there is differential expression of antisense RNA, the enrichment will be observed by a higher signal from the Cy3 label when compared to the Cy5 label.

Figure 6:
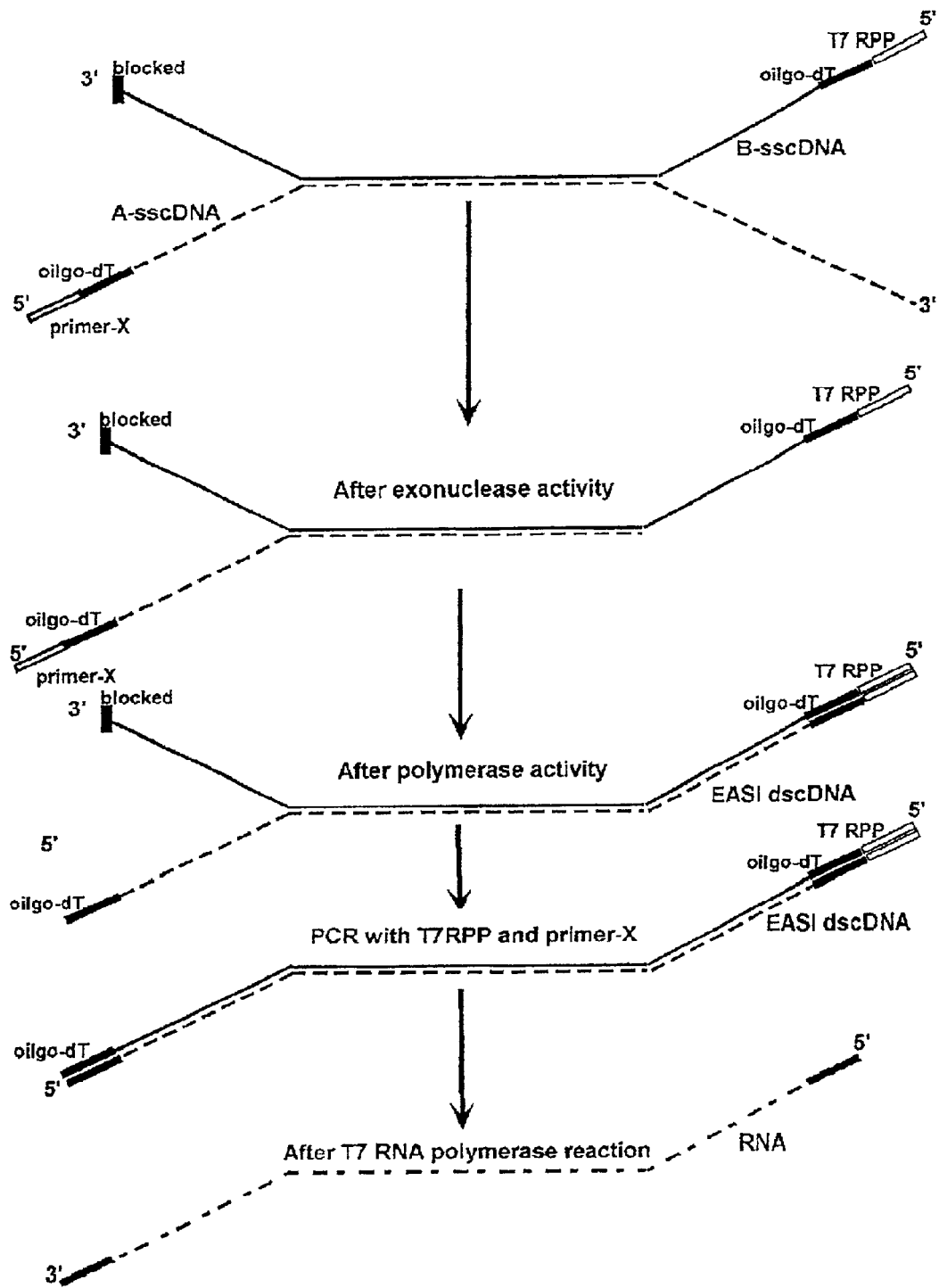
FIG. 6 shows a schematic presentation of a variation of the second embodiment shown in FIG. 5, where a 3'-end of the B-ssc DNA is blocked.
Figure 7:
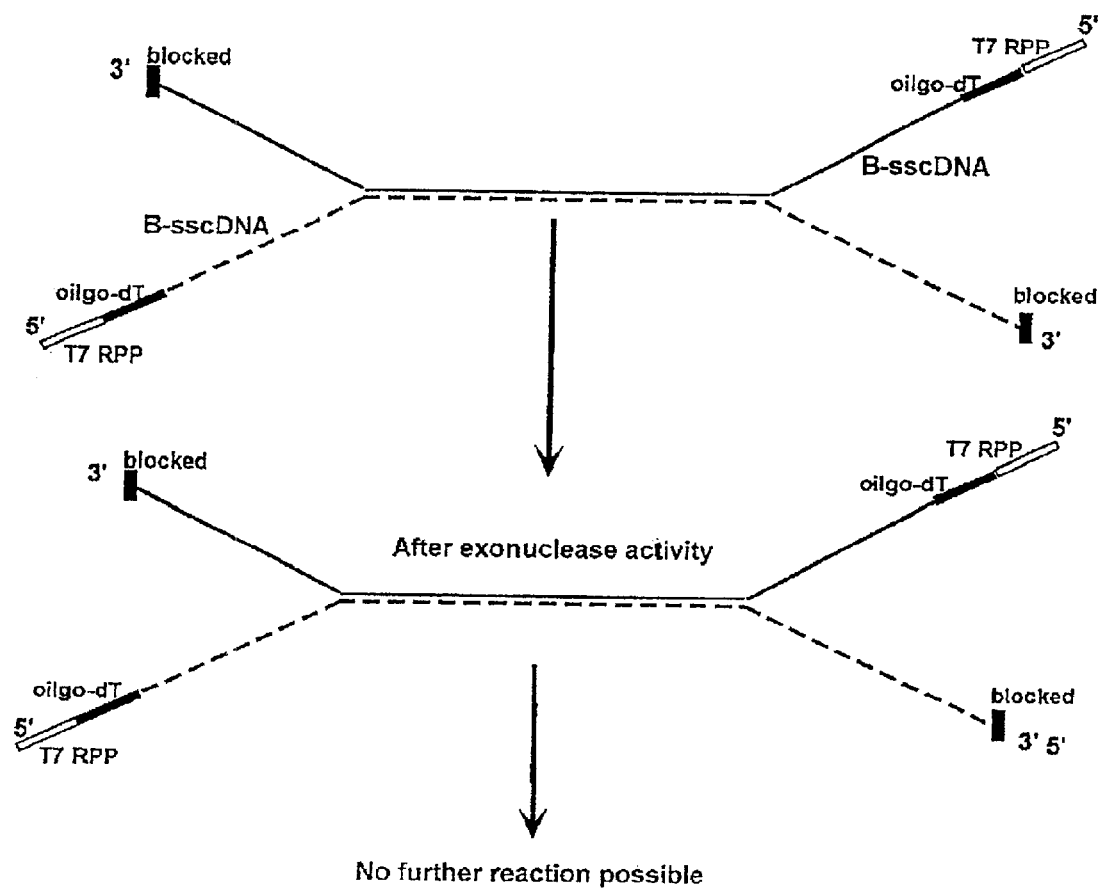
FIG. 7 shows a schematic presentation of hybrids generated that are resistant to the antisense enrichment procedure according to the present invention.

One limitation of this approach is that the analysis cannot disclose the pattern of differential expression, namely, in which population is sense over-expressed and in which is antisense over-expressed. The following provides one way to circumvent this limitation. After the production of sscDNA from B-RNA, the 3' end is blocked by the addition of a nucleotide analog such as deoxynucleoside [1-thio] triphosphate. Such an analog can be added by using the enzyme terminal deoxy transferase (TdT) or by ligating a primer that includes deoxynucleoside [1-thio] triphosphate analogs, to the 3' end with an appropriate ligase (e.g., T4 RNA ligase) that also ligates oligonucleotides to single stranded DNA. Another option is to incorporate such analogs into the sscDNA during the reverse transcription reaction. Once such modified sscDNA, carrying the T7RPP on its 5' end, is produced, it will be resistant to the exonuclease activity of the T4 DNA polymerase during the subsequent EASI reaction. Using this modification approach only sscDNA templates which are unmodified, coming from the A-RNA population, will be templates for the EASI procedure. Hybrids of sense and antisense cDNA derived from B-RNA will be completely resistant to the EASI procedure and will not be represented in the enriched population of EASI cDNA (FIG. 7). The only population of cDNA that will be meaningful is the one that has the T7RPP on one side (FIG. 6).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. In is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

References

Bedford M, Arman E, Orr U A and Lonai P (1995) Analysis of the Hoxd-3 gene: structure and localization of its sense and natural antisense transcripts. DNA Cell. Biol. 14: 295–304.

Chang Y, Spicer D B and Sonenshein G E (1991) Effects of IL-3 on promoter usage, attenuation and antisense transcription of the c-myc oncogene in the IL-3-dependent Ba/F3 early pre-B cell line. Oncogene 6: 1979–1982.

Farrell C M and Lukens L N (1995) Naturally occurring antisense transcripts are present in chick embryo chondrocytes simultaneously with the down regulation of the alpha 1 (I) collagen gene. J. Biol. Chem. 270: 3400–3408.

Fu X D and Maniatis T (1992) Isolation of a complementary DNA that encodes the mammalian splicing factor SC35. Science 256: 535–538.

Khochbin S and Lawrence J (1989) An antisense RNA involved in p53 mRNA maturation in murine erythroleukemia cells induced to differentiate. EMBO J. 8: 4107–4114.

Kimelman D and Kirchner M W (1989) An antisense mRNA directs the covalent modification of the transcript encoding fibroblast growth factor in *Xenopus* oocytes. Cell 59: 687–696.

Krystal G W, Armstrong B C and Battey J F (1990) N-muc mRNA forms an RNA-RNA duplex with endogenous antisense transcripts. Mol. Cell. Bio. 10: 4180–4191.

Lankenau S, Corces V G and Lankenau D H (1994) The *Drosophila* micropia retrotransposon encodes a testes specific antisense RNA complementary to reverse transcriptase. Mol. Cell. Biol. 14: 1764–1775.

Lee R C, Feinbaum R L and Ambros V (1993) The *C. elegans* heterochronic gene lin-4 encodes small RNAs with antisense complementarity to lin-14. Cell 75: 843–854.

Michael N L, Vahey M T, d'Arcy L Ehrenberg P K, Mosca J D, Rappaport J and Redfield R R (1994) Negative-strand RNA transcripts are produced in human immunodeficiency virus type 1 infected cells and patients by a novel promoter down-regulated by Tat. J. Virol. 68: 979–987.

Murphy P R and Knee R S (1994) Identification and characterization of an antisense RNA transcript (gfg) from the human basic fibroblast growth factor gene. Mol. Endocrinol. 8: 852–859.

Noguchi M, Miyamoto S, Silverman T A and Safer B (1994) Characterisation of an antisense Inr element in the eIF-2a gene. J. Biol. Chem. 269: 29161–29167.

Vanhee-Brossollet C and Vaquero C (1998) Do natural antisense transcripts make sense in eukaryotes? Gene 211: 1–9.

What is claimed is:

1. A method for detection of differential expression of natural antisense messenger RNA (mRNA), comprising:

(a) separately obtaining polyA-mRNA-A molecules from cell population A and polyA-mRNA-B molecules from cell population B;

(b) separately generating by a reverse transcription enzyme a population of single-stranded cDNA-A molecules from polyA-mRNA-A and a population of single-stranded cDNA-B molecules from polyA-mRNA-B, wherein the polydeoxythymidine containing oligonucleotide primer used to produce the cDNA-B molecules comprises a specific bacteriophage RNA polymerase promoter region close to its 5' terminus;

(c) incubating the combined populations of single-stranded cDNA-A molecules and single-stranded cDNA-B molecules, under conditions allowing hybridization of sense cDNA molecules with antisense cDNA molecules, wherein each single-stranded antisense cDNA molecule that hybridizes has a segment complementary to the sense cDNA molecule and hybridizes thereto to form a hybrid molecule with a double-stranded segment;

(d) treating the hybrid molecules with a DNA polymerase having a 5' to 3' polymerase activity and a 3' to 5' exonuclease activity to remove single-stranded non-hybridized segments of the hybrid molecule from 3' to 5' and to extend the double-stranded segment of the hybrid molecule 5' to 3' over an adjacent single-stranded segment as template, thereby forming a double-stranded molecule having the RNA polymerase promoter region close to one terminus;

(e) using the double-stranded molecule as a template for the specific RNA polymerase to a population of RNA molecules;

(f) labeling with a first label the RNA molecules produced in step (e);

(g) labeling with a second label as control the polyA-mRNA-A molecules and/or the polyA-mRNA-B molecules of step (a);

(h) mixing labeled RNA molecules from steps (f) and (g) and hybridizing them to a DNA microarray, and (i) identifying the genes on the microarray which are preferentially labeled with the labeled RNA molecules of step (f), wherein the genes so identified on the microarray are detected as differentially expressed natural antisense mRNA.

2. The method according to claim 1, wherein the specific bacteriophage polymerase is selected from the group consisting of T7 RNA polymerase, T3 RNA polymerase, and SP6 RNA polymerase.

3. The method according to claim 1, wherein following step (b) the cDNA-B is modified in order to resist the 3' to 5' exonuclease activity of step (d).

4. The method according to claim 3, wherein in step (d) the 3' terminus of the cDNA-B is modified.

5. The method according to claim 3, wherein in step (d) the entire cDNA-B is modified.

6. The method according to claim 4, wherein 3' terminus of the cDNA-B is modified by addition of a nucleotide analog.

7. The method according to claim 5, wherein the entire cDNA-B is modified by incorporation of nucleotide analogs.

8. The method according to claim 1, wherein the first label of step (f) is Cy3, and the second label of step (g) is Cy5.

9. The method according to claim 1, wherein the first label of step (f) is Cy5, and the second label of step (g) is Cy3.

10. A method for detection of differential expression of natural antisense messenger RNA (mRNA), comprising:

(a) separately obtaining polyA-mRNA-A molecules from cell population A and polyA-mRNA-B molecules from cell population B;

(b) separately generating by a reverse transcription enzyme a population of single-stranded cDNA-A molecules from polyA-mRNA-A and a population of single-stranded cDNA-B molecules from polyA-mRNA-B, wherein the polydeoxythymidine containing oligonucleotide primer used to produce the cDNA-A molecules comprises close to its 5' terminus a sequence identical to an amplification primer used in step (e) and wherein the polydeoxythymidine containing oligonucleotide primer used to produce the cDNA-B molecules comprises a specific bacteriophage RNA polymerase promoter region close to its 5' terminus;

(c) incubating the combined populations of single-stranded cDNA-A molecules and single-stranded cDNA-B molecules, under conditions allowing hybridization of sense cDNA molecules with antisense cDNA molecules, wherein each single-stranded antisense cDNA molecule that hybridizes has a segment complementary to the sense DNA molecule and hybridizes thereto to form a hybrid molecule with a double-stranded segment;

(d) treating the hybrid molecules with a DNA polymerase having a 5' to 3' polymerase activity and a 3' to 5' exonuclease activity to remove single-stranded non-hybridized segments of the hybrid molecule from 3' to 5' and to extend the double-stranded segment of the hybrid molecule 5' to 3' over an adjacent single-stranded segment as template, thereby forming a double-stranded molecule having the RNA polymerase promoter region close to one terminus;

(e) amplifying the double-stranded molecule of step (d) using a thermostable polymerase and a first amplification primer identical to the sequence used in step (b) and a second amplification primer identical to the specific bacteriophage RNA polymerase promoter region of step (b);

(f) using the double-stranded molecules so produced as a template for the specific RNA polymerase to produce a population of RNA molecules;

(g) labeling with a first label the RNA molecules produced in step (f);

(h) labeling with a second label as control the polyA-mRNA-A molecules and/or the polyA-mRNA-B molecules of step (a);

(i) mixing labeled RNA molecules from steps (g) and (h) and hybridizing them to a DNA microarray; and (j) identifying the genes on the microarray which are preferentially labeled with the labeled RNA molecules of step (g).

11. The method according to claim 10, wherein the specific bacteriophage polymerase is selected from the group consisting of T7 RNA polymerase, T3 RNA polymerase, and SP6 RNA polymerase.

12. The method according to claim 10, wherein following step (b) the cDNA-B is modified in order to resist the 3' to 5' exonuclease activity of step (d).

13. The method according to claim 12, wherein in step (d) the 3' terminus of the cDNA-B is modified.

14. The method according to claim 12, wherein in step (d) the entire cDNA-B is modified.

15. The method according to claim 13, wherein 3' terminus of the cDNA-B is modified by addition of a nucleotide analog.

16. The method according to claim 14, wherein the entire cDNA-R is modified by incorporation of nucleotide analogs.

17. The method according to claim 10, wherein the first label of step (g) is Cy3, and the second label of step (h) is Cy5.

18. The method according to claim 1, wherein the first label of step (g) is Cy5, and the second label of step (h) is Cy3.

* * * * *

SEQUENCE LISTING

```
<160> NUMBER OF SEQ ID NOS: 29

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide primer
<221> NAME/KEY: misc_feature
<222> LOCATION: (40)..(40)
<223> OTHER INFORMATION: n is a, c, g or t.

<400> SEQUENCE: 1
ttctagaatt cagcggccgc tttttttttt ttttttttvn                           40

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 2
gatgggagtt gtgtgtttag tc                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 3
```

-continued ggagagagaa gtgcagagtt cg                                    22

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 4
ttagtacaaa cttagggctc t                                     21

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 5
tcatggcaac tccagagcag                                       20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
accacagtcc atgccatcac                                       20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 7
tccaccaccc tgttgctgta                                       20

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 8
ggagttagtc cttgaccact ag                                    22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 9
gcacttacac agttagtcat gg                                    22

<210> SEQ ID NO 10
<211> LENGTH: 188
<212> TYPE: DNA
<213> ORGANISM: Artificial Sequence

```
<220> FEATURE:
<223> OTHER INFORMATION: PCR Amplified Sequence

<400> SEQUENCE: 10
gggcgggccg cttttttttt tttttttttg gagttagtcc ttgaccacta gtttgatgcc    60
atctccattt tgggtgacct gtttcaccag caggcctgtt actctccatg actaactgtg   120
taagtgctta aaatggaata aattgctttt ctacataacc ccaaaaaaaa aaaaaaaaa    180 gcggccgc                                                            188

<210> SEQ ID NO 11
<211> LENGTH: 169
<212> TYPE: DNA
<213> ORGANISM: Artificial Sequence
<220> FEATURE:
<223> OTHER INFORMATION: PCR Amplified Human

<400> SEQUENCE: 11
tttttttttt ttttttttgg agttagtcct tgaccactag tttgatgcca tctccatttt   60
gggtgacctg tttcaccagc aggcctgtta ctctccatga ctaactgtgt aagtgcttaa  120
aatggaataa attgcttttc tacataaccc caaaaaaaaa aaaaaaaa               169

<210> SEQ ID NO 12
<211> LENGTH: 550
<212> TYPE: DNA
<213> ORGANISM: Artificial Sequence
<220> FEATURE:
<223> OTHER INFORMATION: PCR Amplified Human
<221> NAME/KEY: misc_feature
<222> LOCATION: (115)..(115)
<223> OTHER INFORMATION: n is unknown.
<221> NAME/KEY: misc_feature
<222> LOCATION: (189)..(189)
<223> OTHER INFORMATION: n is unknown.
<221> NAME/KEY: misc_feature
<222> LOCATION: (320)..(320)
<223> OTHER INFORMATION: n is unknown.
<221> NAME/KEY: misc_feature
<222> LOCATION: (331)..(331)
<223> OTHER INFORMATION: n is unknown.
<221> NAME/KEY: misc_feature
<222> LOCATION: (341)..(341)
<223> OTHER INFORMATION: n is unknown.
<221> NAME/KEY: misc_feature
<222> LOCATION: (369)..(369)
<223> OTHER INFORMATION: n is unknown.
<221> NAME/KEY: misc_feature
<222> LOCATION: (377)..(377)
<223> OTHER INFORMATION: n is unknown.
<221> NAME/KEY: misc_feature
<222> LOCATION: (446)..(446)
<223> OTHER INFORMATION: n is unknown.
<221> NAME/KEY: misc_feature
<222> LOCATION: (472)..(472)
<223> OTHER INFORMATION: n is unknown.
<221> NAME/KEY: misc_feature
<222> LOCATION: (497)..(497)
<223> OTHER INFORMATION: n is unknown.
<221> NAME/KEY: misc_feature
<222> LOCATION: (538)..(538)
<223> OTHER INFORMATION: n is unknown.

<400> SEQUENCE: 12
ttttcattgt cataattttt tattatgtat caaattgtct tcaatataag ttacaacttg    60
attaaagttg atagacattt gtatctattt aaagacaaaa aaattctttt atgtncaata   120
tcttgtctag agtctagcaa atatagtacc tttcattgca ggatttctgc ttaatataac   180
aagcaaaanc aaacaactga aaaatataaa accaaagcaa accaaacccc ccgctcaact   240
```

```
acaaatgtca atattgaatg aagcattaaa agacaaacat aaagtaactt cagcttttat      300
ctagcaatgc agaatgaatn ctaaaattag nggcaaaaaa ncaaacaaca aacaacaaac      360
aaaacaaanc aaacaancaa aaatcccac caatcttcat gggtaaactt tcctgctcag       420
ggatgtaagc tgactctaga ccattngcgg ttcctgcgga tagcacagcc angatcatct     480
gaagatcatg ccaaatntca tgaccacggc aatgccgatg ccctgcgcc gatgatgngg      540 aatttattgg                                                            550

<210> SEQ ID NO 13
<211> LENGTH: 491
<212> TYPE: DNA
<213> ORGANISM: Artificial Sequence
<220> FEATURE:
<223> OTHER INFORMATION: PCR Amplified Human

<400> SEQUENCE: 13 ttttttttt tttttttctt gctgcagcaa cgcgagtggg agcaccagga tctcgggctc        60
ggaacgagac tgcacggatt gttttaagaa aatggcagac aaaccagaca tgggggaaat     120
cgccagcttc gataaggcca agctgaagaa acggagacg caggagaaga acaccctgcc      180
gaccaaagag accattgagc aggagaagcg gagtgaaatt tcctaagatc ctggaggatt     240
tcctaccccc atcctcttcg agaccccagt cgtgatgtgg aggaagagcc acctgcaaga    300
tggacacgag ccacaagctg cactgtgaac ctgggcactc cgtgccgatg ccaccggcct    360
gtgggtctct gaagggaccc cccccaatc ggactgccaa attctccggt ttgccccggg     420
atattataga aaattatttg tatgaataat gaaaataaaa cacacctcgt ggcaaaaaaa    480
aaaaaaaaaa a                                                          491

<210> SEQ ID NO 14
<211> LENGTH: 206
<212> TYPE: DNA
<213> ORGANISM: Artificial Sequence
<220> FEATURE:
<223> OTHER INFORMATION: PCR Amplified Human

<400> SEQUENCE: 14 ttttttttt tttttttgg gagtggtagg atgaaacaat ttggagaaga tagaagtttg         60
aagtggaaaa ctggaagaca gaagtacggg aaggcgaaga aaagaataga gaagataggg     120
aaattagaag ataaaaacat acttttagaa gaaaaaagat aaatttaaac ctgaaaagta     180
ggaagcagaa aaaaaaaaaa aaaaaa                                           206

<210> SEQ ID NO 15
<211> LENGTH: 206
<212> TYPE: DNA
<213> ORGANISM: Artificial Sequence
<220> FEATURE:
<223> OTHER INFORMATION: PCR Amplified Human
<221> NAME/KEY: misc_feature
<222> LOCATION: (55)..(55)
<223> OTHER INFORMATION: n is unknown.

<400> SEQUENCE: 15
ttttctgtgg ggccatcact ttattaaggg gtcatctaga aggtgggccc cctgncaaac       60
cgcgggactg tgatcgggct ccagctactt caccaccccg ggccagcctg ctccagggt      120 cccttcctgc tgagagcagg cgagaggcag tcaggctcat gaagcagcca ccgggtttgg     180
ctcactggaa ggaatcacac tggaaa                                          206
```

<210> SEQ ID NO 16
<211> LENGTH: 178
<212> TYPE: DNA
<213> ORGANISM: Artificial Sequence
<220> FEATURE:
<223> OTHER INFORMATION: PCR Amplified Human

<400> SEQUENCE: 16
tttttttttt ttttttttct gtgtccactg gagagcttga gctcacactc aaagatcaga      60
ggacctacag agagggctct ttggtttgag gaccatggct tacctttcct gcctttgacc     120
catcacaccc catttcctcc tctttccctc tccccgctgc caaaaaaaaa aaaaaaa       178

<210> SEQ ID NO 17
<211> LENGTH: 127
<212> TYPE: DNA
<213> ORGANISM: Artificial Sequence
<220> FEATURE:
<223> OTHER INFORMATION: PCR Amplified Human
<221> NAME/KEY: misc_feature
<222> LOCATION: (89)..(89)
<223> OTHER INFORMATION: n is unknown.
<221> NAME/KEY: misc_feature
<222> LOCATION: (112)..(112)
<223> OTHER INFORMATION: n is unknown.

<400> SEQUENCE: 17
gaattcgatg cgtattctgt ggcccgccat ctgcgcaggg tggtggtatt ctgccattta      60
cacacgtcgt tctaattaaa aagcgaatna tactccaaaa aaaaaaaaaa angcggccgt     120
tgaattc                                                              127

<210> SEQ ID NO 18
<211> LENGTH: 115
<212> TYPE: DNA
<213> ORGANISM: Artificial Sequence
<220> FEATURE:
<223> OTHER INFORMATION: PCR Amplified Human

<400> SEQUENCE: 18
gaattcagcg gccgcttttt tttttttttt tcttcgaagt gtttaccccca gtgtttgaaa      60 gggattccag atggtcaaat aaaaaaaatg ttcctaaact tggtgatatg aactc         115

<210> SEQ ID NO 19
<211> LENGTH: 204
<212> TYPE: DNA
<213> ORGANISM: Artificial Sequence
<220> FEATURE:
<223> OTHER INFORMATION: PCR Amplified Human
<221> NAME/KEY: misc_feature
<222> LOCATION: (28)..(28)
<223> OTHER INFORMATION: n is unknown.

<400> SEQUENCE: 19
gaattcaggg ccgttctggt tctctctntc tccccgccct ccctcaccac cagtggaacc      60
ttcatcgagt tccacaaacc tggattttttt atgtacaacc ctgaccgtgg ccgtttgcta    120
tattcctttt tctatgaaat aatgtgaatg ataataaaac agctttgact tgaaaaaaaa    180
aaaaaaaaag cggccgctga attc                                           204

<210> SEQ ID NO 20
<211> LENGTH: 109
<212> TYPE: DNA
<213> ORGANISM: Artificial Sequence

```
<220> FEATURE:
<223> OTHER INFORMATION: PCR Amplified Human

<400> SEQUENCE: 20
gaattccctc cccctccttg tgccttcttt gtatataggc ttctcacggc gaccaataaa       60
cagctcccag tttgtatgca aaaaaaaaaa aaaagcggcc gctgaattc                  109

<210> SEQ ID NO 21
<211> LENGTH: 191
<212> TYPE: DNA
<213> ORGANISM: Artificial Sequence
<220> FEATURE:
<223> OTHER INFORMATION: PCR Amplified Human

<400> SEQUENCE: 21
gaattcagcg gccgcttttt ttttttttt ttgggagaag tgtataaatt attatgttga        60
caagcagaga aagaaaagtt aaataccaga taagctttg atttttgtat tgtttgcatc      120
cccttgccct caataaataa agttcttttt tagttccaaa aaaaaaaaaa aaaaagcgg      180 ccgctgaatt c                                                          191

<210> SEQ ID NO 22
<211> LENGTH: 106
<212> TYPE: DNA
<213> ORGANISM: Artificial Sequence
<220> FEATURE:
<223> OTHER INFORMATION: PCR Amplified Human

<400> SEQUENCE: 22
gaattcagcg gaaaaccttg agttctggat tgcctgtgag gattacaaga agatcaagtc       60
ccctgccaag atggctgaga aggcaaagca aatttatgaa gaattc                     106

<210> SEQ ID NO 23
<211> LENGTH: 63
<212> TYPE: DNA
<213> ORGANISM: Artificial Sequence
<220> FEATURE:
<223> OTHER INFORMATION: PCR Amplified Human

<400> SEQUENCE: 23
gaattcaatg ggtaaataaa tgctgctttg gggaaaaaaa aaaaaaagc ggccgctgaa        60 ttc                                                                    63

<210> SEQ ID NO 24
<211> LENGTH: 586
<212> TYPE: DNA
<213> ORGANISM: Artificial Sequence
<220> FEATURE:
<223> OTHER INFORMATION: PCR Amplified Human
<221> NAME/KEY: misc_feature
<222> LOCATION: (527)..(527)
<223> OTHER INFORMATION: n is unknown.

<400> SEQUENCE: 24
tttttttttt ttttttggc ctgggaatga gaaaataact ttatttcatt gtggggagcg        60
ggccgatgtc cagcctcaga acttctggaa ctgcttcttg gtgccggcag ccttggtgac      120
cttgagcacg ttgaagcgca ctgtcttgct cagaggccgg cactcgccca ctgtgacgat      180
gtcaccgatc tggacgtccc tgaagcaggg ggacaggtgt acagacatgt tcttgtggcg      240
cttctcgaag cggttgtact tgcggatgta gtgcagatag tctcggcgga tgacaatggt      300
cctctgcatc ttcatcttgg tcaccacgcc agagaggatc cgccctcgaa tggacacatt      360
```

```
accaagtgaa ggggcatttc ttgtcaatgt aggtgccctc aatagcctcc ttgggtgtct    420
tgaagcccag accgatgttc ttgtagtacc gcgggagctt ctccttgcca gtttctccca    480
gcaggaccct cttcttgttt tgaaagatgg tcggctgctt tggtangca cgctcagtct    540 gaatgtccgc catcttcccg ggcgcctgaa aaaaaaaaa aaaaaa                    586
```

<210> SEQ ID NO 25
<211> LENGTH: 363
<212> TYPE: DNA
<213> ORGANISM: Artificial Sequence
<220> FEATURE:
<223> OTHER INFORMATION: PCR Amplified Human

<400> SEQUENCE: 25

```
tttttttttt ttttttttcc ggcggtgacg acctacgcac acgagaacat gcctctcgca     60
aaggatctcc ttcatccctc tccagaagag gagaagagga acacaagaa gaaacgcctg    120 gtgcagagcc ccaattccta cttcatggat gtgaaatgcc caggatgcta taaaatcacc    180
acggtcttta gccatgcaca aacggtagtt ttgtgtgttg gctgctccac tgtcctctgc    240
cagcctacag gaggaaaagc aaggcttaca gaaggatgtt ccttcaggag gaagcagcac    300
taaaagcact ctgagtcaag atgagtggga aaccatctca ataaacacat tttggataaa    360
ccg                                                                  363
```

<210> SEQ ID NO 26
<211> LENGTH: 563
<212> TYPE: DNA
<213> ORGANISM: Artificial Sequence
<220> FEATURE:
<223> OTHER INFORMATION: PCR Amplified Human

<400> SEQUENCE: 26

```
tttttttttt ttttttcctt cagcgaggcg gccgagctgg ttggtggcgg cggtcgtgcg     60
gacgcaaaca tgcagatctt tgtgaagacc ctcactggca aaaccatcac ccttgaggtc    120
gagcccagtg acaccattga gaatgtcaaa gccaaaattc aagacaagga gggtatccca    180
cctgaccagc agcgtctgat atttgccggc aaacagctgg aggatggccg cactctctca    240
gactacaaca tccagaaaga gtccaccctg cacctggtgt tgcgcctgcg aggtggcatt    300
attgagcctt ctctccgcca gcttgcccag aaatacaact gcgacaagat gatctgccgc    360
aagtgctatg ctcgccttca ccctcgtgct gtcaactgcc gcaagaagaa gtgtggtcac    420
accaacaacc tgcgtcccaa gaagaaggtc aaataaggtg gttctttcct tgaagggcag    480
cctcctgccc aggccccgtg gccctggagc ctcaataaag tgtcccttc  attgactgga    540 gcagcaaaaa aaaaaaaaaa aaa                                            563
```

<210> SEQ ID NO 27
<211> LENGTH: 662
<212> TYPE: DNA
<213> ORGANISM: Artificial Sequence
<220> FEATURE:
<223> OTHER INFORMATION: PCR Amplified Human
<221> NAME/KEY: misc_feature
<222> LOCATION: (316)..(316)
<223> OTHER INFORMATION: n is unknown.
<221> NAME/KEY: misc_feature
<222> LOCATION: (584)..(584)
<223> OTHER INFORMATION: n is unknown.
<221> NAME/KEY: misc_feature
<222> LOCATION: (633)..(633)
<223> OTHER INFORMATION: n is unknown.

<400> SEQUENCE: 27

```
tttttttttt ttttttttgg gactttcagc cccttttaatt aggtgctctg agaagaggtc    60
agaatggcag gcagggggtg gggaaggcgg tgcttcttga gccccactta gcaactggtc   120
actcatcctc tggcagctgg atcttgctgg ggtcgaagca gttggattcc atgatgggaa   180
ggccattggc ctctcggtat ttcacaagcc tctcagcttc gcggcgggac cactctttca   240
tcccatccca cgctcttgga caccctgtgc acctgtagtc aggcagatag gccacaaagg   300
tgctgccaag gaccangatg atggagacgc caaagaagaa gacaagtcgc atgttccaaa   360
cgtccaaaaa cgggggccct gtcataacca atggggaatc cggggtcctc ccatacaagt   420
tttcgtcctc gggttctggg tcctcttgcc acggtgtggt cggttctggg ggccgctttc   480
ccgccacagc ggacggggcg accacaatcc tggagaaact agattcccaa cgggacgccg   540
gcgggccggg aaccctcgcg tcgccgctgc cgccaaaaga ccgngaacgc tcaaccaaac   600
agccaaccgc aagacaaatg gtgctgaagg tcncagggcg ggaaagaaaa aaaaaaaaaa   660
aa                                                                 662
```

<210> SEQ ID NO 28
<211> LENGTH: 504
<212> TYPE: DNA
<213> ORGANISM: Artificial Sequence
<220> FEATURE:
<223> OTHER INFORMATION: PCR Amplified Human

<400> SEQUENCE: 28

```
tttttttttt ttttttttgg cttgactcag gatttaaaaa ctggaacggt gaaggtgaca    60
gcagtcggtt ggagcgagca tcccccaaag ttcacaatgt ggccgaggac tttgattgca   120
cattgttgtt tttttaatag tcattccaaa tatgagatgc gttgttacag gaagtccctt   180
gccatcctaa aagccacccc acttctctct aaggagaatg gcccagtcct ctcccaagtc   240
cacacagggg aggtgatagc attgctttcg tgtaaattat gtaatgcaaa attttttttaa   300
tcttcgcctt aatactttttt tattttgttt tattttgaat gatgagcctt cgtgccccc    360
cttccccctt ttttgtcccc caacttgaga tgtatgaagg cttttggtct ccctgggagt   420
gggtggaggc agccagggct tacctgtaca ctgacttgag accagttgaa taaaagtgca   480
cacctgaaaa aaaaaaaaaa aaaa                                          504
```

<210> SEQ ID NO 29
<211> LENGTH: 66
<212> TYPE: DNA
<213> ORGANISM: Artificial Sequence
<220> FEATURE:
<223> OTHER INFORMATION: Synthetic

<400> SEQUENCE: 29

```
tctagtcgac ggccagtgaa ttgtaatacg actcactata gggcgttttt tttttttttt    60
tttttt                                                              66
```